(12) United States Patent
Hohsaka et al.

(10) Patent No.: US 7,385,038 B2
(45) Date of Patent: Jun. 10, 2008

(54) NON-NATURAL LABELED AMINO ACID AND METHOD OF CONSTRUCTING AMINO ACID/TRNA COMPLEX

(75) Inventors: Takahiro Hohsaka, 27-1, Sumiyoshi-machi, Nonoichi-machi, Ishikawa-gun, Ishikawa (JP) 921-8813; Masahiko Sisido, Okayama (JP)

(73) Assignees: Protein Express Co., Ltd., Choshi-shi (JP); Takahiro Hohsaka, Ishikawa-gun (JP)

( * ) Notice: Subject to any disclaimer, the term of this patent is extended or adjusted under 35 U.S.C. 154(b) by 862 days.

(21) Appl. No.: 10/490,508

(22) PCT Filed: Jul. 15, 2003

(86) PCT No.: PCT/JP03/08970

§ 371 (c)(1),
(2), (4) Date: Mar. 24, 2004

(87) PCT Pub. No.: WO2004/009709

PCT Pub. Date: Jan. 29, 2004

(65) Prior Publication Data

US 2007/0117181 A1    May 24, 2007

(30) Foreign Application Priority Data

Jul. 18, 2002   (JP) .............................. 2002-209736

(51) Int. Cl.
  *C07K 16/00* (2006.01)
(52) U.S. Cl. .................. 530/388.2; 514/44; 435/91.51; 424/23
(58) Field of Classification Search ..................... None
See application file for complete search history.

(56) References Cited

FOREIGN PATENT DOCUMENTS

| JP | 10-330299 | | 12/1998 |
|---|---|---|---|
| JP | 2001-139596 | | 5/2001 |
| WO | 00/13026 | | 3/2000 |
| WO | WO 00/13026 | * | 3/2000 |
| WO | WO-00/13026 | * | 3/2000 |
| WO | 01/19841 | | 3/2001 |

OTHER PUBLICATIONS

Hohsaka, et al., J. Am. Chem. Soc., 1999, 121, 34-40.*
Hecht, 1978, Journal of Biological Chem., 253, 4517-4520.*
Hohsaka, T. et al., "Efficient Incorporation of Nonnatural Amino Acids with Large Aromatic Groups into Streptavidin in In Vitro Protein Synthesizing Systems", J. Am. Chem. Soc., 1999, vol. 121, No. 1, pp. 34 to 40.
Hohsaka, T. et al., "Incorporation of Nonnatural Amino Acids into Streptavidin through In Vitro Frame-Shift Suppression", J. Am. Cehm. Soc., 1996, vol. 118, No. 40, pp. 9778 to 9779.
Hirao, I. et al., "An unnatural base pair for incorporating amino acid analogs into proteins", nature biotechnology, Feb. 2002, vol. 20, pp. 177 to 182.

* cited by examiner

*Primary Examiner*—Anish Gupta
*Assistant Examiner*—Satyanarayana R. Gudibande
(74) *Attorney, Agent, or Firm*—Oblon, Spivak, McClelland, Maier & Neustadt, P.C.

(57) ABSTRACT

This invention relates to: a labeled amino acid that can be introduced into a protein with the aid of a protein synthesis system; a functional protein having functions derived from a label compound; a labeled amino acid comprising an aromatic ring bound to an amino acid side chain and a label compound bound thereto via the aromatic ring; a functional protein to which the labeled amino acid has been introduced; and a novel method for effectively obtaining a labeled amino acid-tRNA complex.

2 Claims, 6 Drawing Sheets

SEQUENCE LISTING

```
<160> NUMBER OF SEQ ID NOS: 3

<210> SEQ ID NO 1
<211> LENGTH: 724
<212> TYPE: RNA
<213> ORGANISM: Artificial Sequence
<220> FEATURE:
<223> OTHER INFORMATION: Description of Artificial Sequence: Artificial
      mRNA for BODIPY FL labeled streptavidin fused with a T7tag and a
      His-Tag.  The sequence from 64 to 96 codes T7tag.  The sequence
      from 112 to 589 codes a streptavidin.
<220> FEATURE:
<223> OTHER INFORMATION: The sequence from 590 to 607 codes a His-Tag.
      The sequence cggg from 358 to 361 codes the BODIPY FL-X-AF.

<400> SEQUENCE: 1
gggagaccac aacgguuucc cucuagaaau aauuuuguuu aacuuuaaga aggagauaua      60
cauauggcua gcaugacugg uggacagcaa auggguaccg aauuccauau ggacccgucc     120
aaggacucca aagcucaggu uucugcagcc gaagcuggua ucacuggcac cugguauaac     180
caacuggggu cgacuuucau ugugaccgcu ggugcggacg gagcucugac uggcaccuac     240
gaaucugcgg uugguaacgc agaaucccgc uacguacuga cuggccguua ugacucugca     300
ccugccaccg auggcucugg uaccgcucug ggcuggacug uggcuuggaa aaacaaccgg     360
gcguaaugcg cacagcgcca cuacgugguc uggccaauac guuggcggug cugaggcucg     420
uaucaacacu caguggcugu uaacauccgg cacuaccgaa gcgaaugcau ggaaaucgac     480
acuaguaggu caugacaccu uuaccaaagu uaagccuucu gcugcuagca uugaugcugc     540
caagaaagca ggcguaaaca acgguaaccc ucuagacgcu guucagcaac accaccacca     600
ccaccacuaa uaaaagcuug aguauucuau aguguccu aaucccagc uugauccggc      660 ugcuaacaaa gcccgaaagg aagcugaguu ggcugcugcc accgcugagc aauaacuagc     720
auaa                                                                 724

<210> SEQ ID NO 2
<211> LENGTH: 647
<212> TYPE: RNA
```

```
<213> ORGANISM: Artificial Sequence
<220> FEATURE:
<223> OTHER INFORMATION: Description of Artificial Sequence: Artificial
      mRNA for BODIPY FL labeled anti-lysozyme camel antibody fused
      with a T7tag and a His-tag.  The sequence from 64 to 96 codes
      T7tag.  The sequence from 112 to 514 codes the anti-lysozyme
      camel antibody.
<220> FEATURE:
<223> OTHER INFORMATION: The sequence cggg from 100 to 103 codes the
      BODIPY FL-X-AF.  The sequence from 515 to 532 codes a His-Tag.

<400> SEQUENCE: 2
gggagaccac aacgguuucc cucuagaaau aauuuuguuu aacuuuaaga aggagauaua      60
cauauggcua gcaugacugg uggacagcaa auggguacuc gggaguaacg aauucgaugu    120
ucagcugcag gcgucgggug uggucucugu ucaggcuggu ggcucccugc gucugucuug    180
ugcagcaucu ggcuacacua uuggcccgua cuguaugggc ugguuucgcc aggcgccggg    240
uaaggaacgu gagggguguug cggcaauuaa caugggguggu ggcaucaccu auuaugcgga    300
cucuguuaag ggucguuuca ccaucucuca ggacaaugcu aagaacacug uguaccugcu    360
gaugaacucu cuggaaccgg aggauacugc gauuuauuau ugugcggcug auucuaccau    420
uuaugcgucc uacaugaauu guggccaugg ccuguccacg gguggcuaug guuaugacuc    480
uuggggucag ggcacucagg uuacuguuuc cucccaccac caccaccacc acuaauaagc    540
uugaguauuc uauagusguca ccuaaaucccc agcuugaucc ggcugcuaac aaagcccgaa    600
aggaagcuga guuggcugcu gccaccgcug agcaauaacu agcauaa                   647

<210> SEQ ID NO 3
<211> LENGTH: 959
<212> TYPE: RNA
<213> ORGANISM: Artificial Sequence
<220> FEATURE:
<223> OTHER INFORMATION: Description of Artificial Sequence: Artificial
      mRNA for biotin-labeled EGFP fused with a T7tag and a His-Tag.
      The sequence from 64 to 96 codes T7tag.  The sequence from 116
      to 826 codes a EGFP, enhanced green fluorescent protein.
<220> FEATURE:
<223> OTHER INFORMATION: The sequence from 827 to 844 codes a His-Tag.
      The sequence cggg from 100 to 103 codes the biotinylated amino
      acids.

<400> SEQUENCE: 3
gggagaccac aacgguuucc cucuagaaau aauuuuguuu aacuuuaaga aggagauaua      60
cauauggcua gcaugacugg uggacagcaa auggguacuc gggaguaacg aauucaguaa    120
aggagaagaa cuuuucacug gaguugucccc aauucuuguu gaauuagaug ugauguuaa    180 ugggcacaaa uuucugucca guggagaggg ugaaggugau gcaacaucg gaaacuuac      240 ccuuaaauuu auuugcacua cuggaaaacu accuguucca uggccaacac uugucacuac    300
uuuaacuuau gguguucaau gcuuuucccg uuauccggau cauaugaaac gcaugacuu    360 uuucaagagu gccaugcccg aagguuaugu acaggaacgc acuauaucuu ucaaagauga    420
cgggaacuac aagacgcgug cugaagucaa guuugaaggu gauacccuug uuaaucguau    480
cgaguuaaaa gguauugauu uuaaagaaga uggaaacauu cucggacaca aacucgagua    540
caacuauaac ucacacaaug uauacaucac ggcagacaaa caaaagaaug gaaucaaagc    600
uaacuucaaa auucgccaca acauugaaga uggauccguu caacuagcag accauuauca    660
acaaaauacu ccaauuggcg auggcccugu ccuuuuacca gacaaccauu accugucgac    720
acaaucugcc cuuuugaaag aucccaacga aaagcgugac cacaugguuc uucuugaguu    780
```

-continued

```
uguaacugcu gcugggauua cacauggcau ggaugagcuc uacaaacacc accaccacca    840
ccacuaauaa gcuugaguau ucuauagugu caccuaaauc ccagcuugau ccggcugcua    900
acaaagcccg aaaggaagcu gaguuggcug cugccaccgc ugagcaauaa cuagcauaa     959
```

NON-NATURAL LABELED AMINO ACID AND METHOD OF CONSTRUCTING AMINO ACID/TRNA COMPLEX

TECHNICAL FIELD

The present invention provides, as a non-natural amino acid, a labeled amino acid in which a label compound is bound directly or via a spacer to an amino acid having an amino acid skeleton with an aromatic ring such as a benzene ring on its side chain. This labeled amino acid is introduced to a protein by utilizing a protein synthesis system, thereby providing a functional protein having functions derived from the label compound with high reproducibility. Further, the present invention relates to a novel method for producing aminoacyl-tRNA, which enables the labeled amino acid to bind effectively to tRNA.

BACKGROUND ART

When a functional group is introduced to a surface of a protein, specific protein residues are generally subjected to chemical modification. This chemical modification is simple, and many specific residues can be advantageously modified at one time. On the contrary, a favorable outcome is hard to attain in respect of the reproducibility of the modification site and/or the regulation of the number of modifications. Because of the progress in recent genetic engineering, it has become possible to substitute amino acid residues in a protein. Modification of a protein synthesis system has enabled the introduction of a desired non-natural amino acid having an amino acid skeleton to a protein and the synthesis of a functional-group-carrying protein with high reproducibility.

In the process of protein synthesis, an amino acid is first bound to the 3' end of tRNA and then transferred to a ribosome where protein synthesis takes place. At the ribosome, codons are translated into amino acids. Use of tRNA comprising a non-natural amino acid bound thereto enables the incorporation of the non-natural amino acid into a protein. P. G. Schuss et al. and A. R. Chamberlain et al. Have reported a method that utilizes a termination codon to incorporate a non-natural amino acid into a protein by allocating UAG termination codon as a genetic code for a non-natural amino acid (Science, 244, p. 182, 1989, J. Am. Chem. Soc., 111, p. 8013, 1989). In this method that utilizes a termination codon, however, two or more kinds of non-natural amino acids cannot be introduced to a protein molecule, and the yield is disadvantageously low.

Sisido et al. Have developed a method that utilizes a four-basecodon in which a codon is comprised of 4 bases. A four-base codon is inserted into a mRNA at the site where a non-natural amino acid is intended to be introduced, an anticodon site of tRNA is substituted with a corresponding four-base, and a non-natural amino acid is then bound thereto. When protein synthesis is conducted using the modified mRNA and the anticodon, in the ribosome, a four-base codon-anticodon pair is formed at the site substituted with a four-base codon of mRNA, and the non-natural amino acid that was bound to tRNA is incorporated into an elongating peptide chain. In contrast, at other sites, triplet (3 bases) is decoded and translated as usual, thus non-natural amino acids are only introduced to the sites designated with a four-base codon in the final protein. Reference can be made to Hohsaka T. et al., J. Am. Chem. Soc., 118, 9778-9779, 1996 and Hohsaka T. et al., J. Am. Chem. Soc., 121, 34-40, 1999 (these documents are cited in this description by reference).

Further, Hirao et al. have developed a protein synthesis system utilizing an artificial base pair (a method that utilizes an artificial base codon) (Hirao, I. et al., Nature Biotech., 20, 177-182, 2002).

In these techniques, a non-natural amino acid can be bound to tRNA by chemical aminoacylation in which a dinucleotide at the 3' end of tRNA is deleted, and a dinucleotide comprising a non-natural amino acid bound thereto is bound with the aid of an RNA ligase instead of the former dinucleotide. Further, more than one non-natural amino acid can be simultaneously introduced to a protein by the method that utilizes a four-base codon and by the method that utilizes an artificial base codon.

Introduction of a non-natural amino acid to a protein has enabled not only the analysis of protein structures and functions but the production of artificial proteins with some type of artificially-added functions. With the use of non-natural amino acids comprising a variety of label substances bound to the amino acid skeletons, therefore, labeled proteins into which the label substances have been incorporated can be obtained. With the method in accordance with each type of label substance, the labeled protein can be detected and/or purified directly or indirectly by means of enzymatic chemical techniques or enzymatic immunochemical techniques when, for example, the label substance is an enzymatic substrate or antigenic substance. This can be utilized in a wide variety of applications in the technical fields associated with medical sciences, pharmaceutical sciences, polymer chemistry, biochemistry, or the like.

It should be noted that a non-natural amino acid cannot be always introduced to a protein by merely binding to tRNA. A natural protein synthesis system has the admissibility of incorporating any of 20 types of naturally-occurring amino acids into a polypeptide chain, regardless of their types. Thus, a natural protein synthesis system is considered to have some degrees of admissibility for non-natural amino acids. However, an amino acid having a side chain with a bulky molecular structure such as 1-pyrenylalanine or ferrocenylalanine cannot be introduced to a protein through the natural protein synthesis system. In a natural protein synthesis system, the ribosome has two sites for incorporating tRNA. tRNA bound to a polypeptide is incorporated into one of them, and tRNA carrying an unreacted amino acid is incorporated into the other site. tRNA carrying a bulky amino acid, however, cannot be incorporated into the ribosome. Thus, tRNA carrying a bulky amino acid is deduced to be incapable of being incorporated into a protein.

Among label compounds, fluorescent substances have particularly high usefulness as labels for a protein. Further, a luminescent substance in the visible light range can be detected by a detector that is extensively and commonly used. Furthermore, a variety of highly sensitive detectors have already been developed and extensively used. These fluorescent substances are very useful as label compounds for labeling cells or the like since they are not affected by interferential actions caused by fluorescence emission in cells. When these fluorescent substances are used as label compounds for non-natural amino acids, however, it is difficult to introduce them to the proteins by a method that utilizes a protein synthesis system due to their large molecular weights. Compounds having a variety of functions, such as enzyme reactivity, antigenicity, protein binding property, or intermolecular interactivity, in addition to fluorescent and luminescent properties, are also useful as label compounds.

The possibility of a label compound being introduced to a protein is disadvantageously limited by the method that utilizes a protein synthesis system due to its molecular weight. It is necessary to resolve this problem in the art.

DISCLOSURE OF THE INVENTION

The present invention provides a labeled amino acid that can be introduced into a protein with the aid of a protein synthesis system. The present invention also provides a functional protein having functions derived from a label compound, wherein the aforementioned functions are attained upon introduction of the labeled amino acid.

Further, the present invention provides a novel method for effectively obtaining a labeled amino acid-tRNA conjugate. This method enables the labeled amino acid to be introduced into a protein via a protein synthesis system.

The present invention relates to the following:

1. a labeled amino acid comprising a label compound bound to an amino acid via an aromatic ring, wherein the aromatic ring is contained in a side chain of a naturally-occurring amino acid or is bound to an amino acid side chain;

2. the labeled amino acid according to 1 above, wherein the amino acid is phenylalanine, tyrosine, tryptophan, or a derivative thereof;

3. the labeled amino acid according to 2 above, wherein the amino acid is aminophenylalanine or a derivative thereof;

4. the labeled amino acid according to any one of 1 to 3 above, wherein a label compound is bound to the aromatic ring at its meta or para position to an amino acid skeleton;

5. the labeled amino acid according to 4 above, wherein a label compound is bound to the aromatic ring at its para position to an amino acid skeleton;

6. the labeled amino acid according to any one of 1 to 5 above, wherein a label compound is bound to an amino acid via a spacer;

7. the labeled amino acid according to any one of 1 to 6 above, wherein the spacer comprises 2 to 18 linearly bound C, O, N, or S atoms or a combination thereof;

8. the labeled amino acid according to 7 above, wherein the spacer comprises 4 to 15 linearly bound C, O, N, or S atoms or a combination thereof;

9. the labeled amino acid according to any one of 1 to 8 above, wherein the label compound is selected from the group consisting of a dye compound, a fluorescent substance, a chemi- or bioluminescent substance, an enzyme substrate, a coenzyme, an antigenic substance, and a protein-binding substance;

10. the labeled amino acid according to 9 above, wherein the label compound is a fluorescent substance;

11. the labeled amino acid according to 10 above, wherein the fluorescent substance has an excitation wavelength and an emission wavelength in the visible light range;

12. the labeled amino acid according to 11 above, wherein the fluorescent substance is a chemical compound comprising 4,4-difluoro-4-bora-3a,4a-diaza-s-indacene as a basic skeleton, a salt thereof, or a derivative thereof;

13. the labeled amino acid according to 11 above, wherein the fluorescent substance is 4,4-difluoro-5,7-dimethyl-4-bora-3a,4a-diaza-s-indacene-3-propionic acid or a salt thereof;

14. a labeled amino acid represented by formula I:

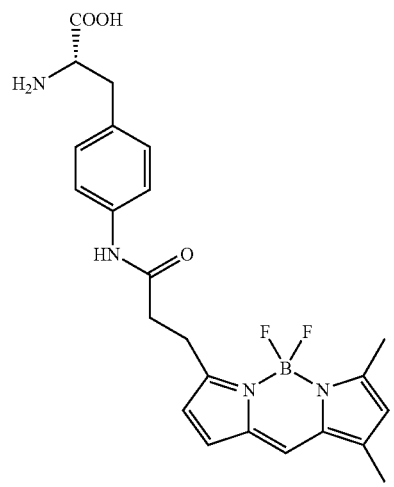

15. a labeled amino acid represented by formula II:

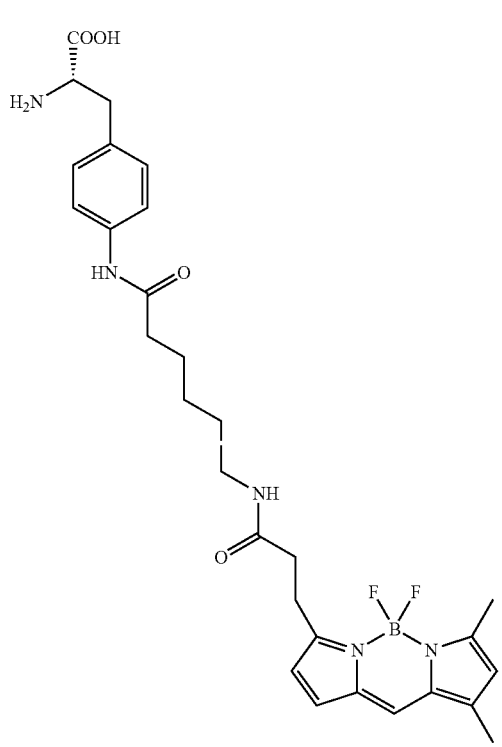

16. the labeled amino acid according to any one of 1 to 15 above, which is bound to pdCpA;

17. a functional protein comprising at least one of the labeled amino acids according to any of 1 to 15 above;

18. the functional protein according to 17 above, wherein the labeled amino acid is labeled with a compound comprising 4,4-difluoro-5,7-dimethyl-4-bora-3a,4a-diaza-s-indacene-3-propionic acid or a salt thereof;

19. a functional protein comprising at least one labeled amino acid according to 14 or 15 above and being labeled with a compound comprising 4,4-difluoro-5,7-dimethyl-4-bora-3a,4a-diaza-s-indacene-3-propionic acid or a salt thereof;

20. the labeled functional protein according to any one of 17 to 19 above, which is an antibody, streptavidin derivative, or green fluorescent protein derivative;

21. the labeled functional protein according to 20 above, which is a derivative of an anti-lysozyme camel antibody;

22. the derivative of an anti-lysozyme camel antibody according to 21 above, wherein fluorescence polarization increases upon binding to a lysozyme molecule, which is an antigen;

23. a method for synthesizing the functional protein comprising the labeled amino acid according to any one of 1 to 15 above, wherein the label compound is introduced via a cell-free protein synthesis system or a protein synthesis system in living cells;

24. the method for synthesizing a functional protein according to 23 above, wherein a method that utilizes a four-base codon, a method that utilizes a termination codon, or a method that utilizes an artificial base codon is used as a protein synthesis system;

25. the method for synthesizing a functional protein according to 24 above, wherein a method that utilizes a four-base codon is used as a protein synthesis system;

26. aminoacyl-tRNA, wherein the labeled amino acid according to any one of 1 to 15 above and tRNA having an anticodon complementary to a codon that is designed to encode the amino acid are bound to each other; and 27. a method for synthesizing the aminoacyl-tRNA according to 26 above, wherein pdCpA is bound to an amino acid, the pdCpA-amino acid conjugate is allowed to react with a label compound to prepare a labeled amino acid-pdCpA conjugate, and the resultant is bound to tRNA(-CA).

The labeled amino acid provided by the present invention can be introduced to a protein via a protein synthesis system to synthesize a labeled protein.

The term "amino acid" used herein refers to, as commonly used, any natural or non-natural compound having a carboxyl group and an amino group in a molecule. The term "labeled amino acid" refers to an amino acid that is bound to a label compound. The "amino acid skeleton" used herein includes a carboxyl group, an amino group, and a portion connecting them in an amino acid.

The term "spacer" used herein refers to a portion that connects an amino acid moiety and a label compound in a labeled amino acid molecule. More specifically, when the amino acid side chain is not directly bound to a label compound in the labeled amino acid molecule and one or more atoms are present between the amino acid side chain and the label compound, the amino acid moiety and the label compound of the labeled amino acid are connected with each other via a spacer. The spacer may comprise at least one of C, O, N, and S atoms in its backbone. The backbone of the spacer comprises 2 to 10, preferably 3 to 8, and more preferably 5, 6, or 7 linearly bound atoms mentioned above, and the linear structure may comprise one or more double-bonds. Further, a spacer may have 1 to several, preferably 1 to 5, and more preferably 1 to 3 cyclic structures such as benzene rings and/or cyclohexyl rings. Alternatively, a combination of cyclic structures such as benzene rings and cyclohexyl rings or a combination of a cyclic structure and the aforementioned linear structure may be sufficient. Specific examples thereof include polyolefins such as polyethylene, polypropylene, polyisobutene, polystyrene, polyvinyl, and polyvinyl chloride, polyethers such as polyoxyethylene, polyethylene glycol, and polyvinyl alcohol, polyamide, polyester, polyimide, polyurethane, and polycarbonate.

Some label compounds should be bound to amino acids via a spacer in order to more effectively exhibit their functions in the proteins to which they have been introduced. In some types of label compounds, for example, steric hindrance toward the label substance in the protein can be decreased if they are bound via a spacer.

Further, the labeled amino acid according to the present invention preferably has an aromatic ring on the side chain of its amino acid moiety, and a label compound is preferably bound to the aromatic ring directly or via a spacer.

The term "aromatic ring" used herein generally refers to every type of unsaturated cyclic compound. Accordingly, it includes a 5- or 6-membered heteroaromatic ring and a polycyclic compound comprising 2 or more, preferably 2 to 5, and more preferably 2 or 3 cyclic structures. A particularly preferable aromatic ring is a benzene ring. Among naturally-occurring amino acids, phenylalanine, tryptophan, and tyrosine are naturally-occurring aromatic amino acids comprising aromatic rings on their side chains. A preferable example of the labeled amino acid of the present invention is a labeled compound in which a label compound is bound to the aromatic ring (either directly or via a spacer).

Binding between an amino acid having an aromatic ring and a label compound and binding between an amino acid having an aromatic ring and a label compound via a spacer may be carried out utilizing the binding between adequate functional groups. A label compound is directly or via a spacer bound to any of a variety of functional groups such as an amino, thiol, carboxyl, hydroxyl, aldehyde, allyl, or halogenated alkyl group of a natural or non-natural amino acid that is not involved in peptide elongation at the time of protein synthesis. Examples of substances that can be used as reagents for labeling amino groups include compounds such as succinimide ester, isothiocyanate, sulfonyl chloride, NBD-halide, and dichlorotriazine. Examples of substances that can be used as reagents for labeling thiol groups include compounds such as alkyl halide, maleimide, and aziridine. Examples of substances that can be used as reagents for labeling carboxyl groups include a diazomethane compound, aliphatic bromides, and carbodiimide. For example, succinimide ester is introduced to a label compound directly or via a spacer, on the other hand, an amino group is introduced to a aromatic ring of an amino acid, and then said amino acid and said label compound can be bound to each other by means of amide bonds. An example of an amino acid comprising an aromatic ring to which an amino group has been introduced is aminophenylalanine. A functional group that is used in such a case can be suitably selected and introduced, and a binding method can also be suitably selected. In this case, performance of amide bond formation at about pH 5 enables selective reaction with an amino group on the side chain of aminophenylalanine even if another amino group is present in the amino acid molecule. Alternatively, another amino group may be protected with Boc or the like, and the protecting group can be removed after the reaction of amino group on the side chain. This technique may be performed by making a reference to, for example, "Shin Seikagaku Jikken Kouza 1, Tanpakushitsu VI, Kouzou Kinou Soukan (New biochemical experimentation 1, Protein VI, Correlation between structure and function)."

In order to prepare labeled functional proteins by applying the labeled amino acid of the present invention to the protein synthesis described below, a specific group necessary for binding to tRNA should be bound to the amino acid. For example, if a dinucleotide (pdCpA) is bound to a carboxyl group of the amino acid, artificial aminoacyl-tRNA can be prepared by binding tRNA lacking a CA dinucleotide at its 3'-terminus (tRNA(-CA)) to the amino acid.

An aromatic ring may be bound to an amino-acid-skeleton-forming atom directly or indirectly via 1, 2, or 3 C, O, N, or S atoms. When an aromatic ring is a benzene ring, a spacer or label compound is more preferably bound to the ring at its para or meta position thereof to the amino acid skeleton from the viewpoint of higher efficiency of incorporation into the ribosome. The para position is particularly preferable.

As mentioned above, a label compound is bound to a functional group of an aromatic ring directly or via a spacer. In the case of aminophenylalanine, para-aminophenylalanine or meta-aminophenylalanine is preferable.

The labeled amino acid of the present invention has properties of its label substance. Accordingly, desired functions can be imparted to the labeled amino acid through the selection of a label compound having desired functions. In the present description, proteins having functions derived from label compounds are referred to as "functional proteins."

Examples of the label compound that is used in the present invention include a dye compound, a fluorescent substance, a chemi- or bioluminescent substance, an enzyme substrate, a coenzyme, an antigenic substance, and a protein-binding substance that are known to persons skilled in the art. Compounds that are used for protein synthesis systems have molecular weights of 1,500 or lower, preferably 1,000 or lower, and more preferably 500 or lower. Examples of fluorescent substances that can be used in the present invention include all known fluorescent substances including rhodamine, fluorescein (FITC), Texas Red, acridine orange, SYBR Green, Cy3, Cy5, a BODIPY compound, and a derivative thereof.

Examples of fluorescent substances that are particularly preferably used in the present invention include a chemical compound comprising 4,4-difluoro-4-bora-3a,4a-diaza-s-indacene as a basic skeleton, a salt thereof, or a derivative thereof (this compounds, a salt thereof, or a derivative thereof is generically referred to as compounds BODIPY herein). A variety of substances having different fluorescent properties for example, BODIPY® FL, BODIPY® TR, BODIPY® R6G, BODIPY® 558/568, and BODIPY® 576/589, are sold by Molecular Probe, Inc. (Oregon, U.S.A.) or other companies. It should be noted that fluorescent substances are not limited to currently commercialized ones.

A chemi- or bioluminescent substance such as luciferin or Lumigen or a derivative thereof can also be used as a label compound in the present invention. A fluorescent label compound preferably has an excitation wavelength and an emission wavelength within the visible light range (approximately 400 to 700 nm). A compound having high emission intensity in an aqueous solution is particularly preferable. A variety of BODIPY compounds have excitation and emission wavelengths within the visible light range. For example, BODIPY FL is excited at 488 nm and exhibits intensive emission within the visible light range. Thus, it can be excited by use of an argon laser. Therefore, BODIPY FL can be easily detected with the use of a common existing apparatus with high sensitivity.

An adequate substance can be selected from among, for example, coenzymes, antigenic substances, and substances that are known to bind to a specific protein in accordance with a function that is intended to be imparted to the target protein, and the selected substance can be used as a label compound in the present invention. A substrate for a specific enzyme (e.g., a substrate for alkaline phosphatase or β-galactosidase) can be detected utilizing coloration caused by the enzyme.

Proteins labeled with an antigenic substance or a substance that is known to bind to a specific protein are advantageous in terms of their usefulness for an indirect detection method that utilizes an antibody or binding protein and ease of purification. For example, a functional protein labeled with biotin by the method of the present invention can bind to avidin or streptavidin with the aid of biotin. With the utilization of this function, a detection system for a specific substance can be established via binding with avidin or streptavidin labeled with a fluorescent compound or the like by the method of the present invention or chemically. In addition, various dyes and a wide variety of substances that can be detected by biochemical, chemical, or immunochemical detection methods can be used as label compounds. This can be understood by those skilled in the art.

A specific aspect of the present invention provides a BODIPY FL-labeled aminophenylalanine derivative (BODIPY FL-AF) having a structure as shown in formula I, wherein a BODIPY commercialized fluorescent dye compound, 4,4-difluoro-5,7-dimethyl-4-bora-3a,4a-diaza-s-indancene-3-propionic acid (BODIPY®-FL), is bound to an aromatic ring on the side chain of aminophenylalanine. This can be introduced into a protein with the aid of a protein synthesis system, and the resulting protein has fluorescent properties of BODIPY (i.e., intensive emission in the visible light range). Thus, it can be easily detected.

Another aspect of the present invention provides BODIPY-labeled amino acids in which BODIPY FL is bound to an amino acid via a portion having a —CO—CH$_2$—CH$_2$—CH$_2$—CH$_2$—CH$_2$—NH— structure derived from BODIPY FL-X as a spacer when a derivative of a BODIPY compound, 6-((4,4-difluoro-5,7-dimethyl-4-bora-3a,4a-diaza-s-indacene-3-propionyl)amino) hexanoic acid (BODIPY®-FL-X), is used as a label compound.

For example, when para-aminophenylalanine is used as an amino acid, BODIPY FL-X-aminophenylalanine (BODIPY FL-X-AF) represented by formula II can be obtained.

In addition to BODIPY FL-X-aminophenylalanine (BODIPY FL-X-AF), BODIPY R6G-AF, BODIPY 576/589-AF, and BODIPY 558/568-AF are also preferable labeled amino acids in the present invention. BODIPY FL-AF and BODIPY 558/568-AF are particularly preferable.

When the labeled amino acid of the present invention is used for the protein synthesis system, aminoacyl-tRNA to which the labeled amino acid of the present invention is bound must be synthesized. Thus, the labeled amino acid of the present invention needs to have a site for binding to tRNA, and an example of the binding site is a dinucleotide (pdCpA). In such a case, pdCpA is previously bound to an amino acid, and an amino acid-pdCpA conjugate may be labeled with a suitable label compound.

For example, AF-pdCpA prepared by binding pdCpA to aminophenylalanine is used as an amino acid, and this amino acid is bound to BODIPY FL-X. This can provide a labeled amino acid-pdCpA (BODIPY FL-X-AF-pdCpA) conjugate having a structure represented by formula III:

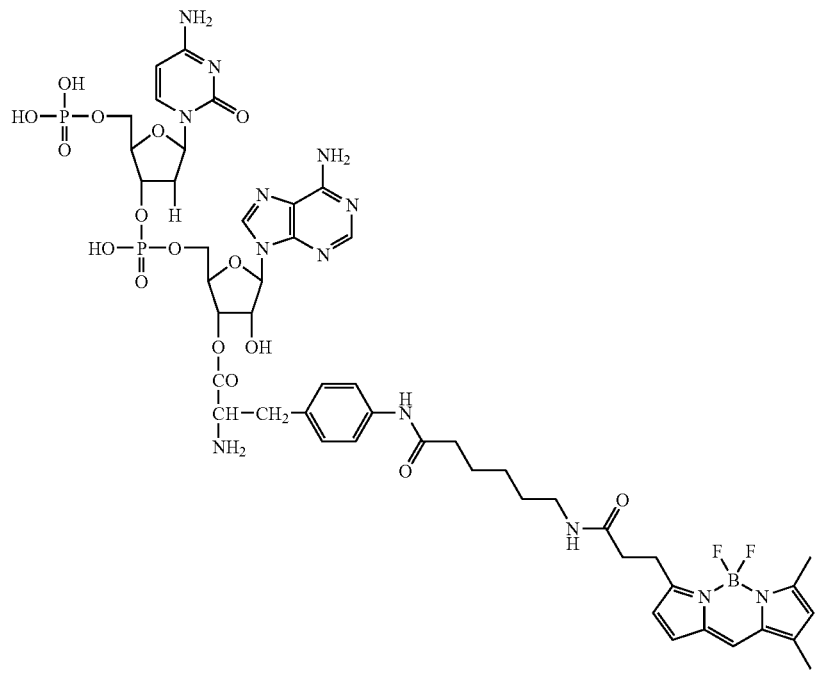

In this compound, aminophenylalanine-pdCpA (AF-pdCpA) is bound to a label compound BODIPY FL via a spacer comprising a site having a —CO—CH$_2$—CH$_2$—CH$_2$—CH$_2$—CH$_2$—NH— structure derived from BODIPY FL-X as mentioned above. This labeled amino acid can also be introduced into a protein through a protein synthesis system, and the resulting protein has fluorescent properties of BODIPY FL (i.e., intensive emission in the visible light range). Thus, it can be easily detected.

Accordingly, BODIPY FL-X is particularly useful for synthesizing the labeled amino acid of the present invention as a label compound comprising the spacer of the present invention.

The aforementioned BODIPY FL-AF or BODIPY FL-X-AF is particularly preferable as the labeled amino acid of the present invention since it has fluorescent properties of BODIPY FL and is effectively incorporated into a protein through a protein synthesis system. For example, when it is compared with BODIPY FL-labeled lysine, i.e., BODIPY FL-K or BODIPY FL-X-K, efficiency of BODIPY FL-AF or BODIPY FL-X-AF of incorporation into a protein is significantly high. A reference may be made to the Examples below.

Incorporation of the labeled amino acid of the present invention into a protein can provide a functional protein comprising the aforementioned labeled amino acid in a desired protein molecule. This protein may be any protein, such as an enzyme or a protein that is capable of binding to a specific molecule such as an antibody or streptavidin.

The present invention also provides a method for synthesizing the aforementioned functional protein. Synthesis of a functional protein in a protein synthesis system necessitates the preparation of aminoacyl-tRNA, wherein the labeled amino acid of the present invention and an anticodon complementary to a codon that is designed to specifically encode the labeled amino acid are bound to each other. Such aminoacyl-tRNA can be synthesized in, for example, the following manner. An amino group of the amino acid is protected with Boc or the like, the protected amino acid is bound to a dinucleotide (pdCpA), the resultant is subjected to deprotection such as removal of Boc, the resulting amino acid-pdCpA conjugate is allowed to react with a label compound to bind a label compound thereto via a functional group introduced in an aromatic ring, and the resulting labeled amino acid-pdCpA conjugate is purified by liquid chromatography. Separately, tRNA lacking a CA dinucleotide at the 3'-terminus (tRNA(-CA)) is prepared, and the labeled amino acid-pdCpA conjugate is bound to the tRNA (-CA) with the aid of a ligase. Thus, aminoacyl-tRNA of interest can be obtained. The present invention includes a method for preparing the labeled amino acid-pdCpA conjugate, wherein an amino acid is bound to pdCpA and is then allowed to react with a label compound to obtain a labeled amino acid-pdCpA conjugate. In conventional techniques, an amino acid is bound to tRNA with the aid of an aminoacyl-tRNA synthase and is then allowed to react with a labeled compound. Or, a labeled amino acid is once synthesized, the synthesized product is then conjugated to pdCpA, and the resultant is further bound to tRNA. In a method for labeling an amino acid-tRNA conjugate, however, it is difficult to distinguish an α-amino group from a side chain amino acid for labeling. Removal of an unreacted amino acid-tRNA conjugate is also difficult. Accordingly, yield of the target labeled amino acid-tRNA conjugate and efficiency of introducing a labeled amino acid into a protein are significantly deteriorated. In general, an aminoacyl-tRNA synthase recognizes an anticodon site of a tRNA. Accordingly, tRNA that is used in the method that utilizes a four-base codon, the method that utilizes an artificial base codon, or the method that utilizes a termination codon cannot be aminoacylated. Only naturally-occurring amino acids can be labeled with this technique. On the other hand, it is necessary to carry out several procedures until the target compound is obtained after the binding of the label compound in a method wherein a labeled amino acid is once synthesized, the synthesized product is then bound to pdCpA, and the resultant is further bound to tRNA. Accordingly, yield per amount of the label compound used becomes significantly low, and thus, this is particularly problematic when an expensive substance such as a fluorescent material is used for labeling. Further, a label substance may be disadvantageously degraded by an acid or base used as a reaction reagent when the labeled amino acid is bound to pdCpA.

In the method for preparing the labeled amino acid-tRNA conjugate of the present invention, an amino acid is allowed to react with a label compound in the final step of the reaction. Thus, a labeled amino acid-pdCpA conjugate can be effectively synthesized. In the case of aminophenylalanine, an α-amino group can be advantageously labeled separately from a side chain amino group when an amino group is bound to an aromatic ring of the side chain. Also, the labeled amino acid-pdCpA conjugate can be completely and easily separated and purified from the unreacted amino acid-pdCpA by liquid chromatography. Since the amino acid is labeled with a label compound in the final step, the conjugates can be easily synthesized with a variety of labeling agents.

The labeled aminoacyl-tRNA prepared by such a method can be produced in a cell-free translation system or a protein synthesis system in living cells. The method that utilizes a four-base codon, the method that utilizes an artificial base codon, or the method that utilizes a termination codon is preferably used as a cell-free translation system. References can be made to Science, 244, p. 182, 1989 and J. Am. Chem. Soc., 111, p. 8013, 1989 concerning the method that utilizes a termination codon, Hirao, I. et al., Nature Biotech., 20, pp. 177-182, 2002 concerning the method that utilizes an artificial base codon, and Hohsaka T. et al., J. Am. Chem. Soc., 118, pp. 9778-9779, 1996 and Hohsaka T. et al., J. Am. Chem. Soc., 121, pp. 34-40, 1999 concerning the method that utilizes a four-base codon. A method in which aminoacyl-tRNA and mRNA are injected into cells by microinjection is a known technique for obtaining a protein comprising a non-natural amino acid through a protein synthesis system in living cells (Science, 268, p. 439, 1995). With this technique, the functional protein of the present invention can be expressed in a living cell.

The method that utilizes a four-base codon is sometimes advantageous since a desired number of labeled amino acids can be introduced into predetermined a protein molecule at its desired positions.

Accordingly, the present invention includes a functional protein that is synthesized by the aforementioned method. Such a functional protein has properties derived from a label compound contained in its molecule. Thus, a wide variety of applications are possible through the utilization of such properties.

For example, a labeled protein having an amino acid labeled with a fluorescent compound is obtained by the method of the present invention, the resulting protein is bound to a substance that is capable of binding thereto, and fluorescence polarization of the conjugate is measured, thereby detecting a substance that is capable of binding to the aforementioned protein. Alternatively, this protein is allowed to react with a chip or plate to which a substance capable of binding thereto has been bound, fluorescence is assayed after washing, or evanescent fluorescence is assayed in an unwashed state. Thus, a substance that is capable of binding to the aforementioned protein can be detected. Further, molecular movement or binding to a specific protein of the aforementioned protein can be directly observed by unimolecular fluorescence detection. Also, the protein is bound to a cell, and a cell having a receptor of the protein is separated by flow cytometry. Alternatively, the protein is incorporated in a cell, and the protein distribution in the cell can be inspected. The functional protein of the present invention can be applied to a variety of fields such as detection of fluorescent changes or inspection of binding to other substances or binding sites by fluorescence correlation spectroscopy. In the examples below, BODIPY FL-labeled derivatives of streptavidin and anti-lysozyme camel antibody are presented as examples of the functional protein of the present invention.

This description includes part or all of the contents as disclosed in the description and/or drawings of Japanese Patent Application No. 2002-209736, which is a priority document of the present application.

BEST MODES FOR CARRYING OUT THE INVENTION

Figure 1:
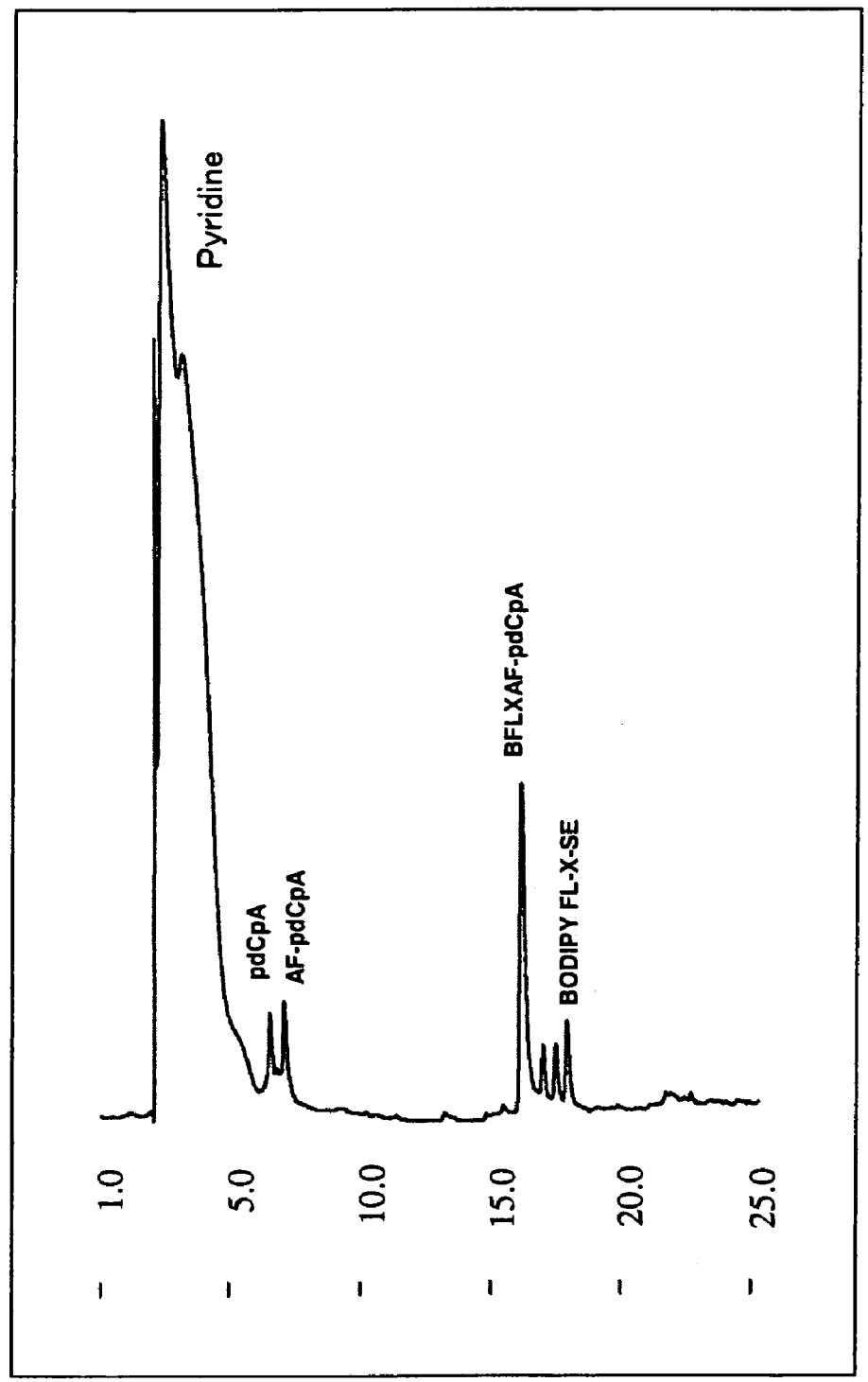
FIG. 1 is a flow chart showing BODIPY FL-X-AF-pdCpA (BFLXAF-pdCpA) isolated by HPLC.

The present invention is hereafter described in greater detail with reference to the following examples, although the present invention is not limited thereto.

Synthesis of BODIPY FL-AF-pdCpA, BODIPY FL-X-AF-pdCpA, BODIPY FL-K-pdCpA, and BODIPY FL-X-K-pdCpA Synthesis of AF-pdCpA di-Boc-aminophenylalanine cyanomethyl ester (1.1 µmol) was added to 5 µl of a solution of pdCpA tetra-n-butylammonium (0.044 µmol/µl) in DMF, and the mixture was allowed to react at room temperature for 2 hours. After the reaction progress was confirmed by HPLC, 1.4 ml of diethyl ether was added to the reaction solution. The resultant was agitated and centrifuged at 15,000 rpm for 5 minutes, and the supernatant was removed. The precipitate was dissolved by adding 20 µl of acetonitrile, 1.4 ml of diethyl ether was added thereto, and the resultant was agitated, followed by centrifugation at 15,000 rpm for 5 minutes. The supernatant was removed, the precipitate was dissolved by adding 20 µl of acetonitrile again, 1.4 ml of diethyl ether was added thereto, and the mixture was agitated, followed by centrifugation at 15,000 rpm for 5 minutes. The supernatant was removed, followed by drying under reduced pressure.

Trifluoroacetic acid (100 µl) was added to the resultant with ice-cooling, the mixture was dissolved with slight agitation, and the product was allowed to stand on ice for 10 minutes. Trifluoroacetic acid was removed under reduced pressure, 1.4 ml of diethyl ether was added thereto, the mixture was agitated and centrifuged, and the supernatant was removed. The product was further washed twice with diethyl ether. After the drying under reduced pressure, the product was dissolved in 40 µl of DMSO.

Synthesis of BODIPY FL-AF-pdCpA and BODIPY FL-X-AF-pdCpA

One microliter (1 µl) of DMSO solution containing 0.1 M BODIPY FL-SE or BODIPY FL-X-SE (Molecular Probes) 7 µl of DMSO, and 16 µl of 0.1 M pyridine-HCl (pH 5.0) were added to 8 µl of a solution of AF-pdCpA in DMSO, and the mixture was allowed to react at 37° C. for 12 hours. Fractions containing a target substance were collected by reversed phase HPLC (eluent: a linear gradient of 0.1% trifluoroacetic acid with methanol, see the HPLC flow chart), and the solvent was removed using a centrifugal concentrator. A part of the resultant was hydrolyzed with 0.1 M NaOH, and released pdCpA was quantified by HPLC, thereby determining the concentration of the recovered target substance. The target substance was dissolved in DMSO to a concentration of 2.2 mM.

Synthesis of BocLys-pdCpA

α-Boc-ε-Nps-lysine cyanomethyl ester (1.1 µmol) was added to 5 µl of a solution of pdCpA tetra-n-butylammonium (0.044 µmol/µl) in DMF, and the mixture was allowed to react at room temperature for 2 hours. After the reaction progress was confirmed by reversed phase HPLC (eluent: a linear gradient of 0.1% trifluoroacetic acid with methanol), 1.4 ml of diethyl ether was added to the reaction solution. The resultant was agitated and centrifuged at 15,000 rpm for 5 minutes, and the supernatant was removed. The precipitate was dissolved by adding 20 µl of acetonitrile, 1.4 ml of diethyl ether was added thereto, and the resultant was agitated, followed by centrifugation at 15,000 rpm for 5 minutes. The supernatant was removed, the precipitate was dissolved by adding 20 µl of acetonitrile again, 1.4 ml of diethyl ether was added thereto, and the mixture was agitated, followed by centrifugation at 15,000 rpm for 5 minutes. The supernatant was removed, and the resultant was dried under reduced pressure.

The resultant was dissolved in 200 µl of a solution comprising 40 mM sodium thiosulfate and 50 mM sodium acetate (pH 4.7), and the solution was allowed to stand at room temperature for 1 hour. A peak of interest was fractionated by reverse phase HPLC, and a solvent was removed using a centrifugal concentrator. The resultant was dissolved in DMSO to a concentration of 3 mM.

Synthesis of BODIPY FL-K-pdCpA and BODIPY FL-X-K-pdCpA

One microliter (1 µl) of DMSO solution containing 0.1 M BODIPY FL-SE or BODIPY FL-X-SE (Molecular Probes), 5 µl of DMSO, and 10 µl of 0.1 M NaHCO$_3$ were added to 5 µl of DSMO solution containing 3 mM BocLys-pd CpA, and the mixture was allowed to react on ice for 30 minutes. The resultant was neutralized with the addition of 1.5 µl of 1 M acetic acid and then diluted with 0.1% TFA. Fractions containing a target substance were collected by reversed phase HPLC (eluent: a linear gradient of 0.1% trifluoroacetic acid with methanol). The solvent was removed using a centrifugal concentrator, and the resultant was dissolved in 50 µl of dioxane. An aqueous solution of 4 M HCL (50 µl) was added, and the resultant was allowed to stand at room temperature for 2 hours. 2M ammonium acetate (50 µl) was added, and fractions containing a target substance were collected by reversed phase HPLC. The solvent was removed using a centrifugal concentrator. A part of the resultant was hydrolyzed with 0.1 M NaOH, and released pdCpA was quantified by reversed phase HPLC, thereby determining the concentration of the recovered target substance. The target substance was dissolved in DMSO to a concentration of 2.2 mM.

Synthesis of Aminoacyl-tRNA

Four microliters (4 µl) of 5× ligation buffer (275 mM HEPES-Na pH 7.5, 75 mM MgCl$_2$, 16.5 mM DTT, and 5 mM ATP), 2.5 µl of 200 µM tRNA (-CA), 2 µl of a solution of aminoacyl-pdCpA in DMSO, 0.4 µl of 0.1% BSA, 1.2 µl of T4 RNA Ligase (25 units/µl), and 9.9 µl of water were mixed, and the mixture was allowed to react at 4° C. for 2 hours. 3M AcOK (pH 4.5, 10 µl) and 70 µl of water were added thereto, and an equivalent amount of phenol/chloroform (1/1) (saturated with 0.3M AcOK (pH 4.5)) was added thereto. The mixture was agitated and centrifuged. The upper phase was recovered, an equal volume of chloroform was added, and the mixture was agitated, followed by centrifugation. The upper phase was recovered, and 300 µl of ethanol was added thereto, the mixture was slightly mixed, and the resultant was then allowed to stand at −20° C. for 1 hour. The mixture was centrifuged at 15,000 rpm at 4° C. for 30 minutes, the supernatant was removed, and 200 µl of 70% EtOH stored at −20° C. was added to the resultant, followed by centrifugation at 15,000 rpm at 4° C. for 5 seconds. The supernatant was removed, and the resultant was dried under reduced pressure. The product was dissolved in 2 µl of 1 mM potassium acetate (pH 4.5).

Figure 2:
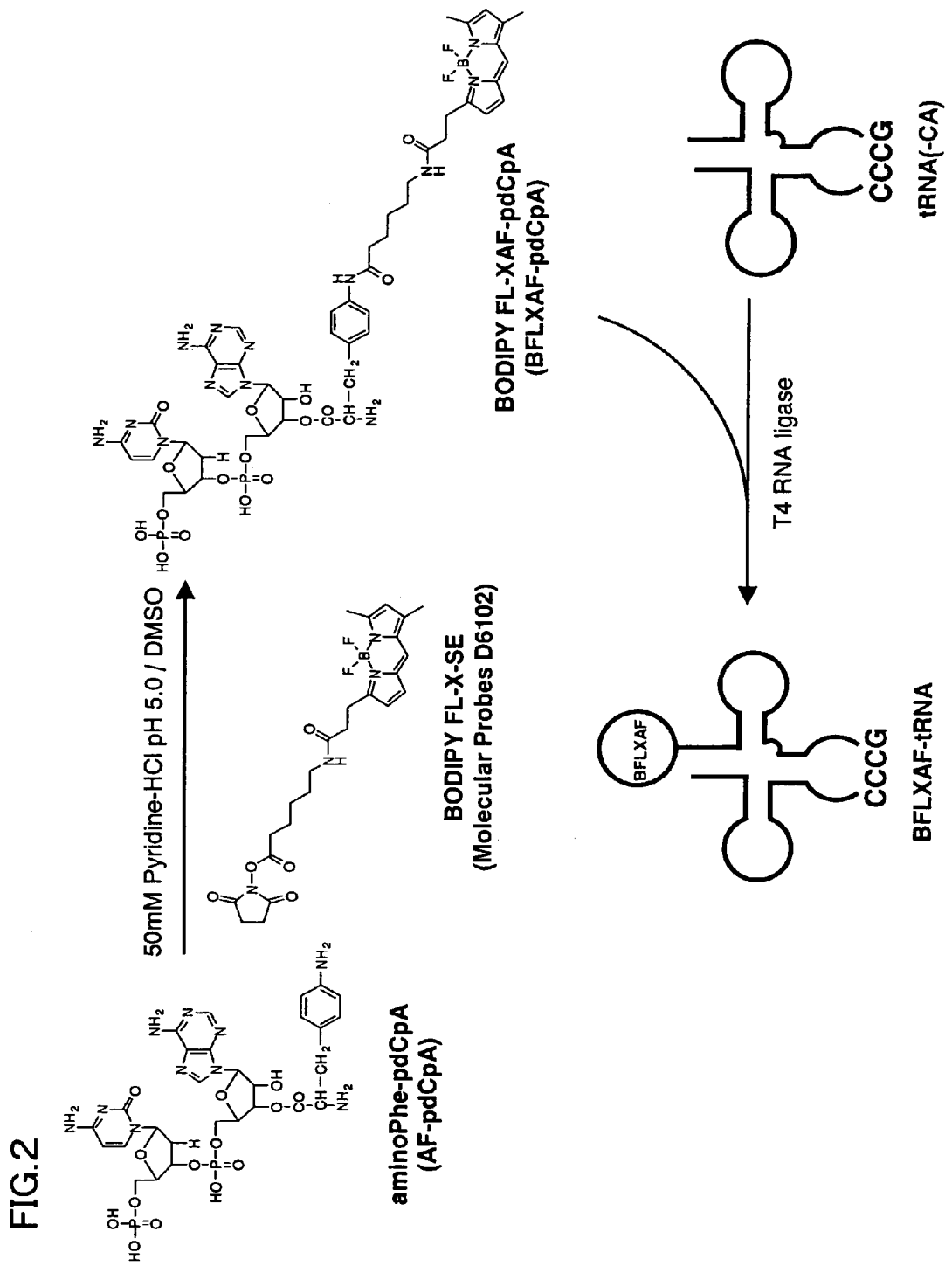
FIG. 2 schematically shows the synthesis of BODIPY FL-X-AF-tRNA.

The above synthesis reaction is schematically shown in FIG. 2 by taking the synthesis of BODIPY FL-X-AF-tRNA as an example.

Figure 3:
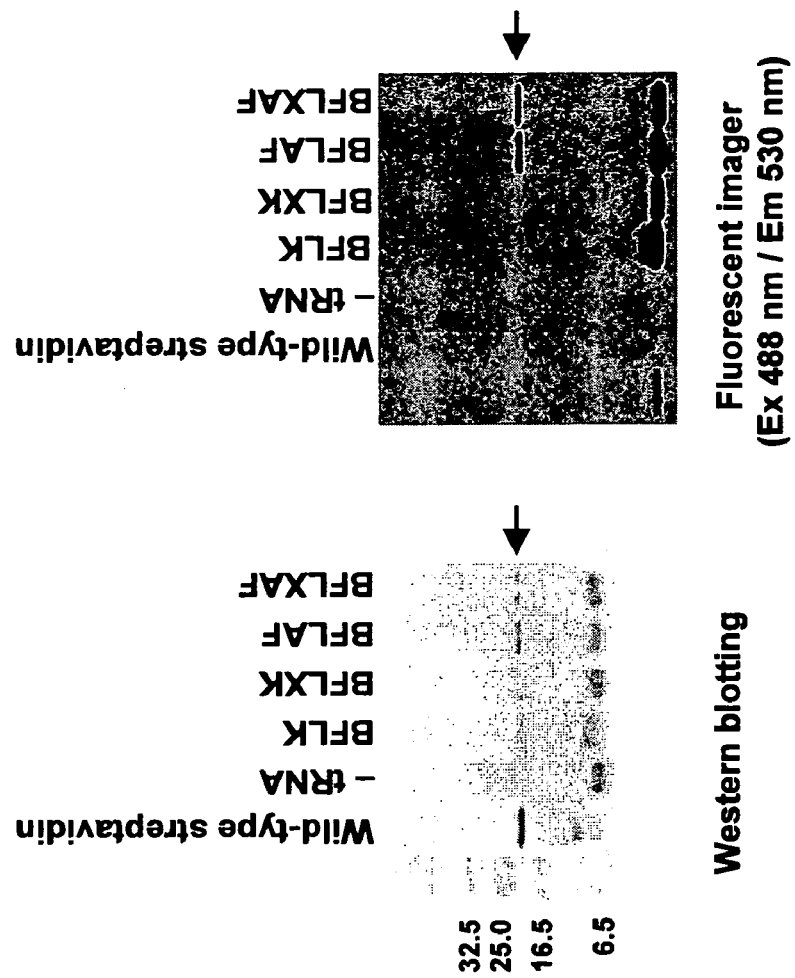
FIG. 3 shows the results of fluorescence detection (right) and Western blotting (left) of the streptavidin generated upon introduction of BODIPY FL-X-AF, BODIPY FL-AF, BODIPY FL-X-K, or BODIPY FL-K into streptavidin by the method that utilizes a four-base codon.

Introduction of BODIPY FL-Labeled Aminophenylalanine or Lysine to the Tyr83 Position of Streptavidin One microliter (1 µl) of HEPES-KOH (55 mM, pH 7.5), 210 mM potassium glutamate, 6.9 mM ammonium acetate, 1.7 mM dithiothreitol, 1.2 mM ATP, 0.28 mM GTP, 26 mM phosphoenolpyruvic acid, 1 mM spermidine, 1.9% polyethylene glycol-8000, 35 µg/ml of folic acid, 12 mM magnesium acetate, 0.1 mM 20 types of amino acids and mRNA (8 µg/µl) of streptavidin containing a T7 tag at the N-terminus and a HisTag at the C-terminus and having the codon at the Tyr83 position being substituted with CGGG encoding the aforementioned labeled amino acid (SEQ ID NO: 1), 2 µl of E. coli extract (Promega), and 1 µl of the aminoacyl-tRNA solution mentioned above were mixed with a reaction solution (10 µl). The resultant was subjected to translation at 37° C. for 1 hour. Water (9 µl) and a 2× sample buffer (10 µl) were added to 1 µl of translation solution, the mixture was heated at 95° C. for 5 minutes, and 5 µl thereof was subjected to 15% SDS-PAGE. After the completion of SDS-PAGE, the resulting gel was observed using a fluorescent scanner (FluorImager 595, Molecular Dynamics, excitation beam: 488 nm, emission filter: 530 DF 30). This gel was subjected to Western blotting using the anti-T7 tag antibody. When translation was carried out with the addition of BODIPY FL-AF-tRNA and BODIPY FL-X-AF-tRNA, a band was observed at the same position with the case of a wild-type streptavidin by Western blotting, and this band emitted fluorescence. Thus, it was confirmed that BODIPY FL-AF (BFLAF) and BODIPY FL-X-AF (BFLXAF) were introduced into the streptavidin. Although introduction of BODIPY FL-K (BFLK) and BODIPY FL-X-K (BFLXK) in the streptavidin was also confirmed, the protein levels therein detected by Western blotting and by a fluorescent scanner were much lower than those detected in the cases of BODIPY FL-AF and BODIPY FL-X-AF. The results of Western blotting and fluorescence detection are shown in FIG. 3.

Figure 4:
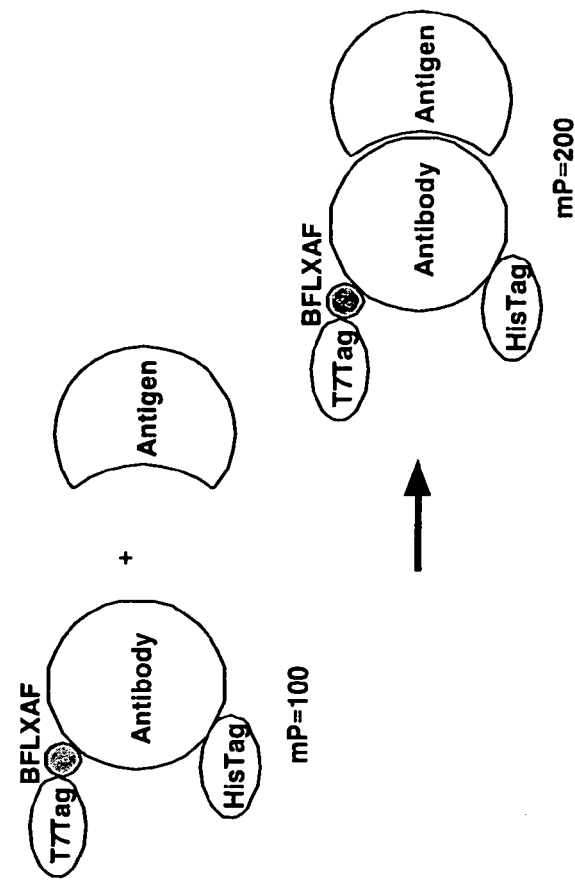
FIG. 4 shows the results of lysozyme quantification by assaying the fluorescence of the anti-lysozyme antibody (camel antibody) to which BODIPY FL-X-AF has been introduced. The right side of the drawing shows a reaction diagrammatically.
Figure 4:
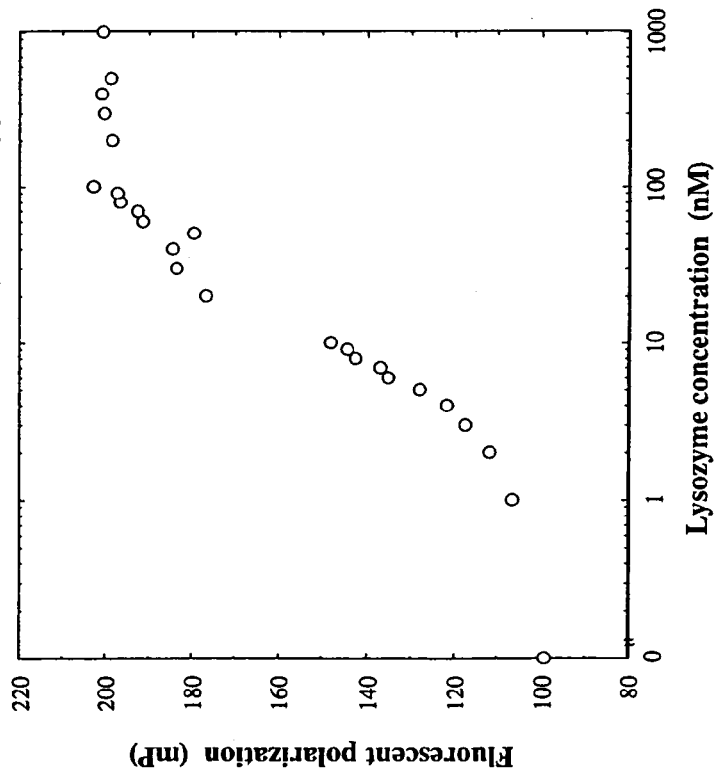

Assay of Fluorescence Polarization mRNA (SEQ ID NO: 2) encoding the anti-lysozyme antibody (derived from a camel) which comprises BODIPY FL-X-AF at its N-terminus and is tagged a T7 Tag and with a HisTag on the N-terminus and the C-terminus respectively was used to conduct translation in the same manner as with the case of the streptavidin in the presence of BODIPY FL-X-AF-tRNA. For the purpose of disulfide bond formation, 2 mM oxidized glutathione was added instead of dithiothreitol. The product was purified through a metal chelate column (TALON, Clontech), and the degree of fluorescence polarization was assayed while adding lysozyme to the eluate using a BEACON 2000 (Panvera). As a result, increase in the degree of fluorescence polarization was observed along with the addition of lysozyme. This phenomenon had occurred because the antigen lysozyme was bound to the anti-lysozyme antibody comprising at its N-terminus BODIPY FL-X-AF, and this inhibited molecular movements, whereby the degree of fluorescence polarization exhibited by BODIPY FL-X-AF was increased. The assay results are shown in FIG. 4.

Synthesis of BODIPY R6G-AF-pdCpA, BODIPY 558/568-AF-pdCpA, and BODIPY 576/589-AF-pdCpA Five microliters (5 μl) of DMSO solution containing 0.1 M BODIPY R6G-SE, BODIPY 558/568-SE, or BODIPY 576/589-SE (Molecular Probes), 15 μl of DMSO, and 20 μl of 0.1 M pyridine-HCl (pH 5.0) were added to 10 μl of a solution of AF-pdCpA in DMSO, and the mixture was allowed to react at 37° C. for 48 hours. Fractions containing a target substance were collected by reversed phase HPLC (eluent: a linear gradient of 0.1% trifluoroacetic acid with methanol), and the solvent was removed using a centrifugal concentrator. The target substance was dissolved in 0.1% trifluoroacetic acid, a part of the resultant was hydrolyzed with 0.1 M NaOH, and released pdCpA was quantified by HPLC, thereby determining the concentration of the recovered target substance. The target substance was dissolved in DMSO to a concentration of 2.2 mM.

Synthesis of BioAF-pdCpA and BioX-AF-pdCpA

Five microliters (5 μl) of DMSO solution containing 0.1 M Biotin-SE or Biotin-X-SE (Sigma), 5 μl of DMSO, and 20 μl of 0.1 M pyridine-HCl (pH 5.0) were added to 10 μl of a solution of AF-pdCpA in DMSO, and the mixture was allowed to react at 37° C. for 24 hours. Fractions containing a target substance were collected by reversed phase HPLC (eluent: a linear gradient of 0.1% trifluoroacetic acid with methanol), and the solvent was removed using a centrifugal concentrator. A part of the resultant was hydrolyzed with 0.1 M NaOH, and released pdCpA was quantified by HPLC, thereby determining the concentration of the recovered target substance. The target substance was dissolved in DMSO to a concentration of 2.2 mM.

Synthesis of BioK-pdCpA and BioX-K-pdCpA

Two microliters (2 μl) of DMSO solution containing 0.1 M Biotin-SE or Biotin-X-SE (Sigma) in 0.1 M DMSO (2 μl), 2 μl of DMSO, and 8 μl of 0.1 M NaHCO$_3$ were added to 4 μl of DMSO solution containing 3 mM BocLys-pdCpA, and the mixture was allowed to react on ice for 30 minutes. The resultant was neutralized by adding 1.2 μl of 1 M acetic acid and then diluted with 0.1% TFA. Fractions containing a target substance were collected by reversed phase HPLC (eluent: a linear gradient of 0.1% trifluoroacetic acid with methanol), and the solvent was removed using a centrifugal concentrator. Trifluoroacetic acid (100 μl) was added with ice-cooling, the mixture was dissolved, and the solution was allowed to stand with ice-cooling for 5 minutes. Trifluoroacetic acid was removed under reduced pressure, 200 μl of water was added thereto, and a part of the resultant was hydrolyzed with 0.1 M NaOH, and released pdCpA was quantified by reversed phase HPLC, thereby determining the concentration of the recovered target substance. After centrifugal concentration, the target substance was dissolved in DMSO to a concentration of 2.2 mM.

Figure 5:
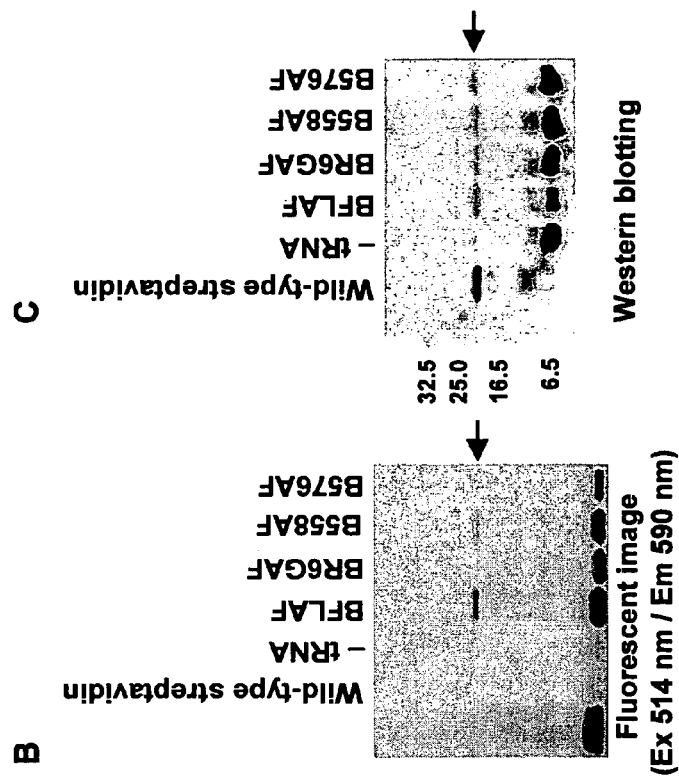
FIG. 5A shows structural formulae of BODIPY FL-AF, BODIPY R6G-AF, BODIPY 558/568-AF, and BODIPY 576/589-AF.
FIG. 5B shows the results of fluorescence detection of streptavidin generated upon introduction thereof separately into streptavidin by the method that utilizes a four-base codon.
FIG. 5C shows the results of Western blotting thereof.
Figure 5:
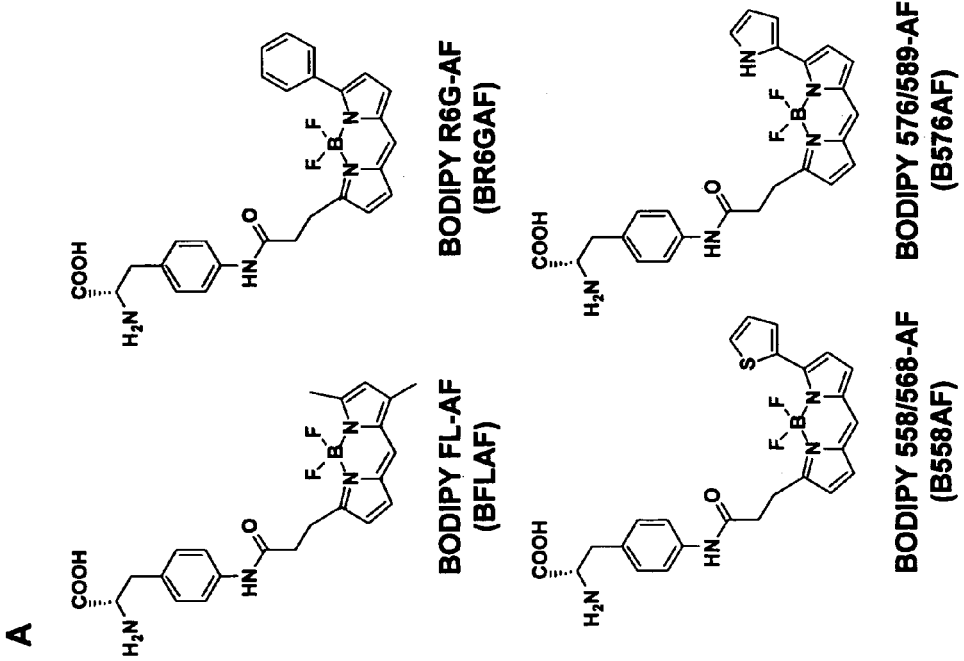

Introduction of BODIPY R6G-, BODIPY 558/568-, and BODIPY 576/589-Labeled Aminophenylalanine to the Tyr83 Position of Streptavidin Similarly with the case of the introduction of BODIPY FL-labeled aminophenylalanine or lysine, translation, SDS-PAGE, and Western blotting were carried out. Fluorescence detection was carried out using an emission filter 590 DF 30 (excitation beam: 514 nm). When translation was carried out with the addition of aminoacyl-tRNA to which BODIPY R6G-AF (BR6GAF), BODIPY 558/568-AF (B558AF), or BODIPY 576/589-AF (B576AF) had been bound, a band was observed at the same position with the case of a wild-type streptavidin by Western blotting, and this band emitted fluorescence. Thus, introduction of these labeled aminophenylalanines in the streptavidin was confirmed. The results of Western blotting and fluorescence detection are shown in FIG. 5.

Figure 6:
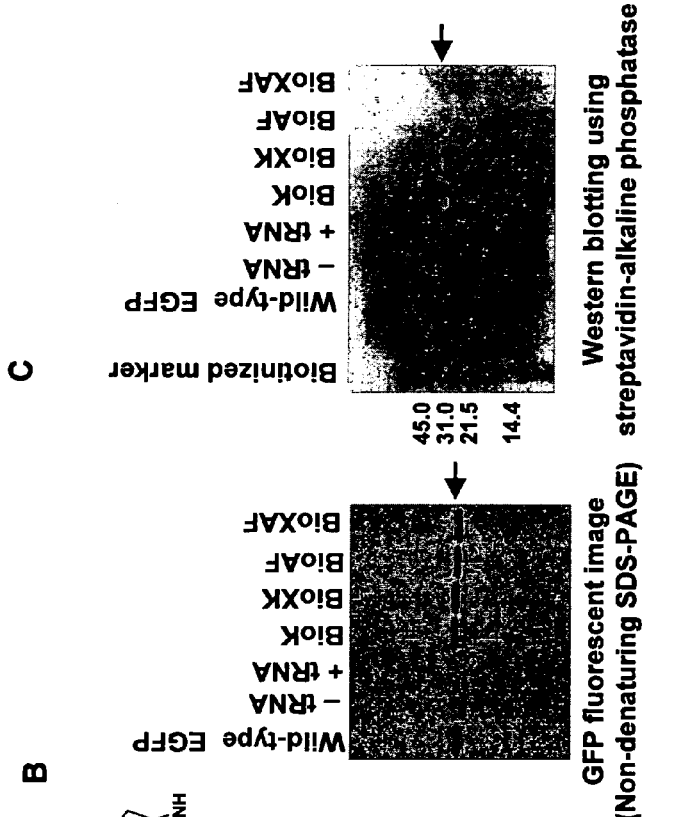
FIG. 6A shows structural formulae of Biotin-Lys, Biotin-X-Lys, Biotin-AF, and Biotin-X-AF.
FIG. 6B shows the results of fluorescence detection of the green fluorescent protein generated upon introduction thereof separately into green fluorescent protein by the method that utilizes a four-base codon.
FIG. 6C shows the results of Western blotting thereof with streptavidin-bound alkaline phosphatase.
Figure 6:
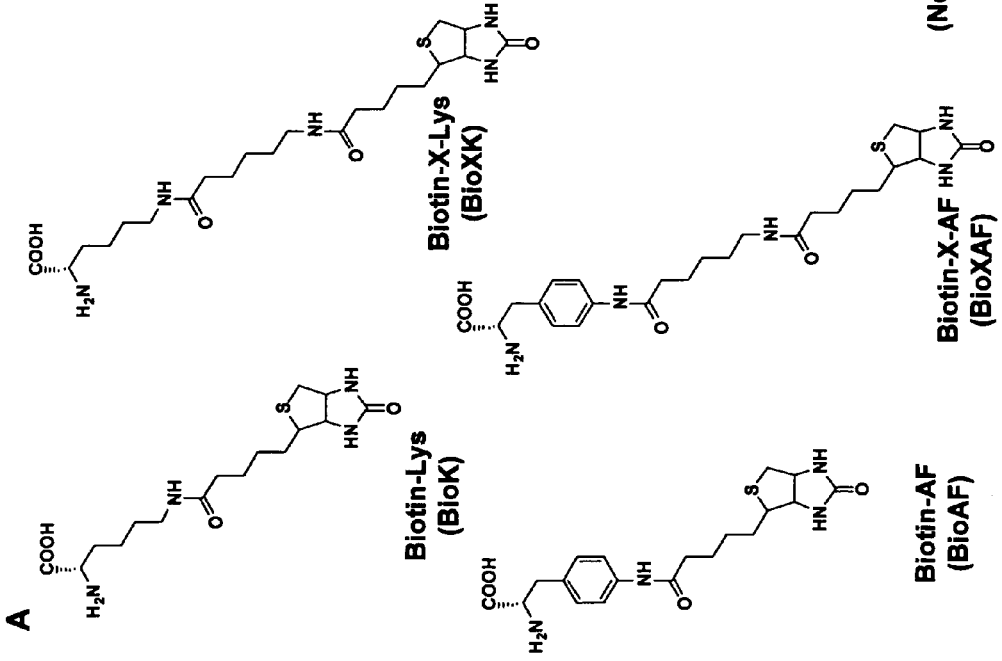

Introduction of Biotin-Labeled Aminophenylalanine or Lysine to the N-Terminus of a Green Fluorescent Protein mRNA of a green fluorescent protein comprising at its N-terminus a T7 Tag and at its C-terminus a HisTag and having the codon at the N-terminus being substituted with CGGG encoding the aforementioned labeled amino acid (SEQ ID NO: 3) and aminoacyl-tRNA to which biotin-labeled aminophenylalanine or lysine had been bound were used to conduct translation and SDS-PAGE similarly with the case of the streptavidin. When the fluorescence of the green fluorescent protein was detected, a sample buffer not containing β-mercaptoethanol was used, and heating was carried out at 50° C. for 5 minutes. Western blotting using the anti-T7 tag antibody was carried out similarly with the case of the streptavidin. Western blotting using the streptavidin-bound alkaline phosphatase was carried out using a mixed solution of 2 μg/ml of streptavidin (Sigma) and 1 μg/ml of biotin-labeled alkaline phosphatase (Calbiochem). When translation was carried out with the addition of aminoacyl-tRNA to which biotin-labeled amino acid had been bound, a band was observed at the same position with the case of a wild-type green fluorescent protein by Western blotting using the anti-T7 antibody (data is not shown), a fluorescent band derived from the green fluorescent protein was observed, and a band was detected by Western blotting using streptavidin-bound alkaline phosphatase. Thus, introduction of biotin-labeled aminophenylalanine or lysine into the protein was confirmed. The results of Western blotting and fluorescence detection are shown in FIG. 6.

All publications, patents, and patent applications cited herein are incorporated herein by reference in their entirety.

INDUSTRIAL APPLICABILITY

The labeled amino acid provided by the present invention is effectively used in a protein synthesis system, and utilization thereof enables a protein having functions derived from a label compound to be effectively synthesized in a protein synthesis system. Accordingly, the present invention provides a novel means for effectively synthesizing a functional protein.

Free Text of Sequence Listing

SEQ ID NO: 1 represents artificial mRNA of a BODIPY FL-labeled streptavidin which is fused with a T7 tag and a His-Tag, wherein a sequence consisting of residues 64 to 96 encodes the T7 tag, a sequence consisting of residues 112 to 589 encodes the streptavidin, a sequence consisting of residues 590 to 607 encodes the His-Tag, and a sequence consisting of residues 358 to 361, CGGG, encodes BODIPY FL-X-AF.

SEQ ID NO: 2 represents artificial mRNA of a BODIPY-FL-labeled anti-lysozyme camel antibody which is fused with a T7 tag and a His-Tag, wherein a sequence consisting of residues 64 to 96 encodes the T7 tag, a sequence consisting of residues 116 to 514 encodes the anti-lysozyme camel antibody, a sequence consisting of residues 515 to 532 encodes the His-Tag, and a sequence consisting of residues 100 to 103, CGGG, encodes BODIPY FL-X-AF.

SEQ ID NO: 3 represents artificial mRNA of a biotin-FL-labeled green fluorescent protein which is fused with a T7 tag and an His-Tag, wherein a sequence consisting of residues 64 to 96 encodes the T7 tag, a sequence consisting of residues 116 to 826 encodes the green fluorescent protein, a sequence consisting of residues 827 to 844 encodes the His-Tag, and a sequence consisting of residues 100 to 103, CGGG, encodes the biotin-labeled amino acid.

The invention claimed is:

1. An aminoacyl-tRNA, wherein tRNA is conjugated to labeled amino acid-pdCpA conjugate and wherein the labeled amino acid-pdCpA conjugate has the structure:

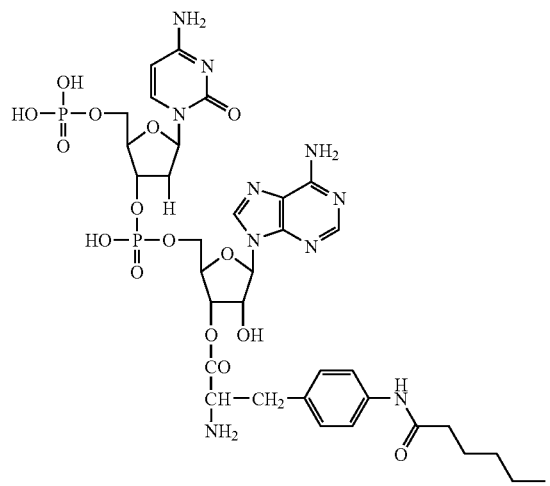

-continued

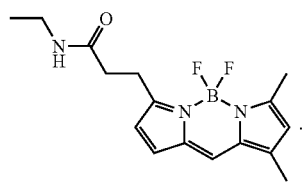

2. A method for synthesizing the aminoacyl-tRNA according to claim 1, wherein pdCpA is bound to an amino acid, the pdCpA-amino acid conjugate is allowed to react with a label compound to prepare a labeled amino acid-pdCpA conjugate, and the resultant is bound to tRNA(-CA).

* * * * *